United States Patent

Koh et al.

[11] Patent Number: 5,506,361
[45] Date of Patent: Apr. 9, 1996

[54] IMIDAZOBENZOQUINONES AND COMPOSITION FOR PREVENTING OR TREATING HYPERTENSION OR CONGESTIVE HEART FAILURE CONTAINING THE SAME

[75] Inventors: Keiko Koh; Hiroshi Kushida, both of Ibaraki; Noriie Itoh, Ibarakik; Kazunori Ozawa, Ibaraki, all of Japan; William W. McWhorter, Jr., Parchment, Mich.

[73] Assignee: TheUpjohn Company, Kalamazoo, Mich.

[21] Appl. No.: 122,445

[22] PCT Filed: Apr. 30, 1992

[86] PCT No.: PCT/US92/03440

§ 371 Date: Oct. 21, 1993

§ 102(e) Date: Oct. 21, 1993

[87] PCT Pub. No.: WO92/19211

PCT Pub. Date: Nov. 12, 1992

[30] Foreign Application Priority Data

| May 8, 1991 | [JP] | Japan | 3-102639 |
| Jun. 12, 1991 | [JP] | Japan | 3-140057 |
| Aug. 16, 1991 | [JP] | Japan | 3-205879 |
| Dec. 27, 1991 | [JP] | Japan | 3-346283 |

[51] Int. Cl.⁶ ............ C07D 403/10; C07D 235/04; A61K 31/41; A61K 31/415
[52] U.S. Cl. .................... 548/253; 548/302.7
[58] Field of Search ............... 548/302.7, 253; 514/318, 394

[56] References Cited

U.S. PATENT DOCUMENTS

| 4,207,324 | 6/1980 | Matsumura et al. | 424/273 |
| 4,340,598 | 7/1982 | Furukawa et al. | 424/273 |
| 4,582,847 | 4/1986 | Furukawa et al. | 514/400 |

FOREIGN PATENT DOCUMENTS

| 0209707 | 1/1987 | European Pat. Off. |
| 253310 | 1/1988 | European Pat. Off. |
| 291969 | 11/1988 | European Pat. Off. |
| 392317 | 10/1990 | European Pat. Off. |
| 399731 | 11/1990 | European Pat. Off. |
| 399732 | 11/1990 | European Pat. Off. |
| 400974 | 12/1990 | European Pat. Off. |
| 400835 | 12/1990 | European Pat. Off. |
| 415886 | 3/1991 | European Pat. Off. |
| 0426021 | 5/1991 | European Pat. Off. |
| 82/98270 | of 0000 | Japan. |
| 54-148788 | 11/1979 | Japan. |
| 56-71073 | 6/1981 | Japan. |
| 58-157768 | 9/1983 | Japan. |

*Primary Examiner*—David B. Springer
*Attorney, Agent, or Firm*—Lawrence T. Welch

[57] ABSTRACT

There are provided pharmacologically active compounds which are highly effective to treat hypertension or congestive heart failure, and are well absorbed into the body and have long-lasting action. Thus, the present invention provides A compound represented by the general formula:

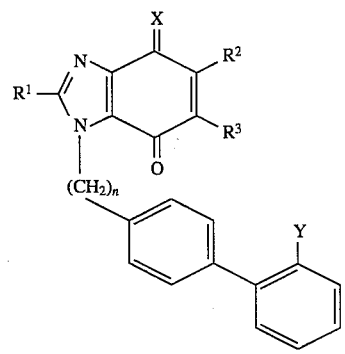

or a pharmacologically acceptable ester or salt thereof, and a pharmaceutical composition for preventing or treating hypertension or congestive heart failure which comprises the compound as an active ingredient.

5 Claims, No Drawings

IMIDAZOBENZOQUINONES AND COMPOSITION FOR PREVENTING OR TREATING HYPERTENSION OR CONGESTIVE HEART FAILURE CONTAINING THE SAME

This application is a 371 of PCT/US 92/03440 filed Apr. 30, 1992.

BACKGROUND OF THE INVENTION

The present invention relates to a novel imidazobezoquinone or a pharmacologically acceptable ester or salt thereof and a pharmaceutical composition for preventing or treating hypertension or congestive heart failure which contains the same as an active ingredient.

It is widely known that Renin-Angiotensin-Aldosterone system is closely connected with hypertensive pathogen or pathemia through control of blood pressure and amount of fluid or electrolyte. Prevention and treatment of hypertension (including essential hypertension) and further congestive heart failure by controlling this system have been studied for a long time. As the controlling methods, there are i) inhibition of synthesis or secretion of renin which is thought to be situated at the most upstream position, ii) inhibition of a reaction between renin and a substrate of renin (angiotensinogen) to decrease angiotensin (I) which is a reaction product, iii) inhibition of an enzyme which converts angiotensin (I) into angiotensin CID having strong vasoconstriction action, aldosterone secretion stimulating action, sympathetic nerve function promoting action and the like (angiotensin converting enzyme: ACE), iv) inhibition of the action of the produced angiotensin CID by blocking a receptor part thereof, v) activation of angiotensinase which rapidly degrades the produced angiotensin (II) and the like.

Among the agents active in this system, the study of ACE inhibitors is most advanced, and many such drugs are used for preventing or treating hypertension or congestive heart failure. However, since the ACE inhibitors are not selective and act toward other systems such as kalliklein-kinin system and the like, there is a clinical problem in that the side effects such as skin rash and dry cough occur more frequently. For this reason, many attempts to develop a renin inhibitor, which is thought to be more selective, have been tried, but have not successfully been marketed.

The putative peptide Angiotensin II antagonist Saralasin has been available for over 30 years. However, its therapeutic use has been severely limited by its partial agonistic action, short plasma half-life and lack of oral activity. Since the discovery of a "non-peptide" Angiotensin H antagonist by Takeda (Japan Kokai Patent 1979—148,788, 1981—71,073, 1982—98,270, 1983—157,768), extensive efforts have been made to modify or optimize this prototype lead especially by Dupont. These are reported in EP-A02533 10 and EP-A0291969, and the compound known as Dup753 is currently being clinically tested. The structure of Dup753 is set out below:

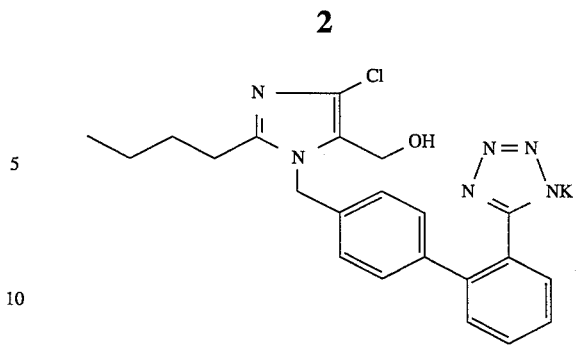

However, since this compound is usually produced as 1:1 positional isomer upon N-alkylation, Dup753 can not be selectively synthesized unless a special process is used, and this is thought to be a problem for mass production. On the other hand, it was thought to be effective at that time that the 5-position of the imidazole should have a polar group for increasing the pharmacological activity. This thinking was compelled to be significantly modified by the finding of benzimidazoles shown in EP-A0392317 (also reported in EP-A-0400835 and EP-A0399732 later). Further, this was developed into imidazopyridines (see EP-A0399731, EP-A0400974 and EP-A0415886). An example of such a structure is shown below:

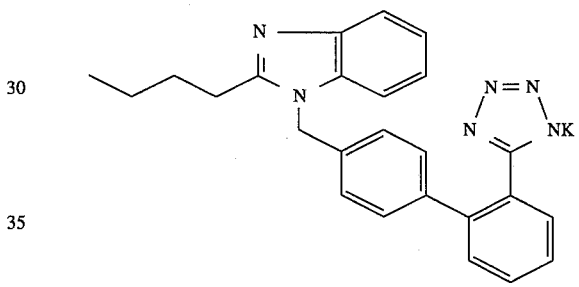

PROBLEMS TO BE SOLVED BY THE INVENTION

From the above described point of view, and paying attention to Ang-II antagonist as an agent for preventing or treating hypertension or congestive heart failure, the present inventors have studied drugs which have higher activity, good absorbability into the body upon oral administration and long-lasting action, and as a result, we have found that certain imidazoquinones are effective, resulting in the present invention.

Common quinone structures in the present invention is similar to those of vitamin A, vitamin K, ubiquinone and the likes, and these are known to have the lipidperoxidation inhibiting action. This shows that having both of Ang-II antagonist and lipidperoxidation inhibiting action works more effectively on treatment of hypertension for a long period of time, taking into consideration that the lipidperoxidation inhibiting action is effective for inhibiting development of arterial sclerosis and there is the closer relationship between arterial sclerosis and hypertension.

INFORMATION DISCLOSURE

A number of imidazo containing moieties are disclosed as useful in the treatment of hypertension as described above, see, e.g., Japanese Kokai 78/148,788; 81/71,073; 82/98,270 and 83/157,768; published European patent applications EPA 253310; 291969; 392317; 400835; 399732; 399731; 4400974; and 415886. EP 400974 discloses imidazoquinones among a wide variety of other possibilities.

SUMMARY OF THE INVENTION

The present invention provides an imidazobenzoquinone represented by the general formula [1]:

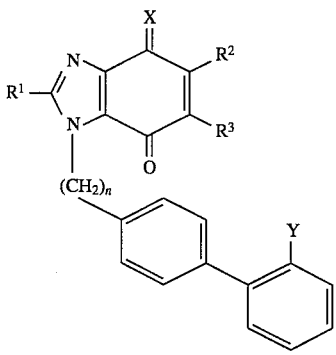

wherein $R^1$ is hydrogen atom, a $C_1$–$C_8$ alkyl group, a $C_2$–$C_8$ alkenyl group, a $C_2$–$C_8$ alkynyl group, —$CF_3$ group, an aryl group or an aralkyl group;

X is oxygen atom or a group of the formula N—$OR^6$, N—$NHR^5$, or $CR_7R^8$;

Y is a 1H-tetrazol-5-yl group or an alkali metal salt thereof, a —$CO_2R^4$ group, a —CONR'R" group or a —$CONHSO_2R^5$ group;

$R^2$ and $R^3$ are independently hydrogen atom, an optionally substituted $C_1$–$C_8$ alkyl group, a $C_1$–$C_8$ alkoxy group, —CN, a —$CO_2^{R4}$ group, a —CONR'R" group or a —$CONHSO_2R^5$ group, or $R^2$ and $R^3$ together form an optionally substituted aromatic or heterocyclic ring;

$R^4$ is hydrogen atom, alkali metal or a $C_1$–$C_8$ alkyl group;

$R^5$ is a $C_1$–$C_8$ alkyl group, a $C_3$–$C_{10}$ cycloalkyl group or an aryl group;

$R^6$ is hydrogen atom or a $C_1$–$C_8$ alkyl group optionally substituted by Y;

$R^7$ and $R^8$ are independently hydrogen, $C_1$–$C_8$ alkyl, $C_2$–$C_8$ alkenyl, $C_2$–$C_8$ alkynyl, $CF_3$, aryl, or aralkyl, or $R^7$ and $R^8$ together form an alicyclic structure, R' and R" are independently hydrogen atom or a $C_1$–$C_8$ alkyl group, or R' and R" together form an alicyclic structure; and n is 0, 1 or 2, or a pharmacologically acceptable ester or salt thereof, and a pharmaceutical composition for preventing or treating hypertension or congestive heart failure which comprises as an active ingredient an imidazobenzoquinone of the general formula [1] or pharmacologically acceptable ester or salt thereof.

EFFECT OF THE INVENTION

According to the present invention, there is provided imidazobenzoqunones which have high activity to hypertension or congestive heart failure, are well absorbed into the body upon administration and have long-lasting action. Further, a pharmaceutical composition for preventing or treating hypertension or congestive heart failure containing the same.

The carbon atom content of the carbon containing moieties is indicated by a prefix "$C_i$–$C_j$" wherein i is the lowest number of carbon atoms and j is the highest number of carbon atoms.

As the lower alkyl group represented by $R^1$ in the general formula [1], there are an alkyl group having from 1 to 8 carbon atoms, for example, methyl, ethyl, n-propyl, isopropyl, n-butyl, isobutyl, t-butyl, n-pentyl, isoamyl, n-hexyl, n-heptyl, n-octyl and the like. As the lower alkenyl group, there are vinyl, 1-propenyl, 2-propenyl, 2-methyl-1-propenyl, 1-butenyl, 2-butenyl, 1-pentenyl, 2-pentenyl, 1-hexenyl, 1-heptenyl, 1-octenyl and the like. As the lower alkynyl group, there are an acetylene group, 1-propynyl, 2-propynyl, 1-butynyl, 2-butynyl, 1-pentynyl, 2-pentynyl, 1-hexynyl, 1-heptynyl, 1-octynyl and the like. As the aryl group or aralkyl group, there are those having from 6 to 10 carbon atoms, for example, phenyl, naphthyl, benzyl, phenethyl, 3-phenylpropyl, 4-phenylbutyl and the like. These aryl or aralkyl groups may be optionally substituted by substituents such as the lower alkyl group described above, or lower alkoxy group, a halogen atom, nitro group, cyano group and the like.

When Y is an alkali metal salt of the 1H-tetrazol-5-yl in the compound represented by the general formula [1], examples of the alkali metal salt are sodium, potassium salt and the like. Examples of $R^4$ in the —$CO_2R^4$ group are a hydrogen atom, an alkali metal, a lower alkyl group. Examples of the alkali metal salt are sodium, potassium salt and the like. Examples of the lower alkyl group are methyl, ethyl, n-propyl, isopropyl, n-butyl, isobutyl, t-butyl, n-pentyl, isoamyl, n-hexyl, n-heptyl, n-octyl and the like. Examples of NR'R" in the —CONR'R" group are amino, methylamino, dimethylamino, ethylamino, diethylamino, n-propylamino, di(n-propyl)amino, diisopropylamino, dibutylamino, pyrrolidinyl, piperazino, morpholino and the like. And examples of $R^5$ in the —$CONHSO_2^{R5}$ group are methyl, ethyl, n-propyl, n-butyl, isobutyl, t-butyl, cyclopentyl, cyclohexyl, phenyl and the like.

When $R^2$ or $R^3$ represents the lower alkyl group, the —$CO_2R^4$ group, the —CONR'R" group or the —$CONHSO_2R^5$ group, examples of them are the same as described above about $R^1$, $R^4$, NR'R" and $R^5$. When $R^2$ or $R^3$ is the substituted lower alkyl group, examples of them are hydroxymethyl, carboxymethyl, 2-carboxyethyl, 3-carboxy-n-propyl, 4-carboxy-n-butyl, 2-hydroxyethyl, 3-hydroxy-n-propyl, 4-hydroxy-n-butyl and the like. Examples of the lower alkoxy are methoxy, ethoxy, n-propoxy, isopropoxy, n-butoxy and the like.

When $R^2$ and $R^3$ taken together represent the aromatic or heterocyclic ring, examples of the aromatic ring are benzene ring or naphthalene ring, and examples of the heterocyclic ring are pyridine ring, pyrimidine ring, furan ring or thiophene ring. These aromatic and heterocyclic rings may be optionally substituted by a halogen atom, a lower alkyl group, $CF_3$, a lower alkoxy group, —CN, a —$CO_2^{R4}$ group, a —COR'R" group, a —$SO_3H$ group or an alkali metal salt thereof, a —$SO_2NHR^5$ group. Examples of these lower alkyl group, lower alkoxy group, —$CO_2R^4$ group, —CONHR'R" group, —$CONHSO_2R_5$ group, —$SO_2NHR^5$ group are the same as those described above.

Further, in the compound of the general formula [2], examples of the lower alkyl group, the lower alkenyl group, the lower alkynyl group, the aryl group and the aralkyl group represented by $R^1$ as well as examples of the lower alkyl group represented by $R^{2'}$ and $R^{3'}$ are as described about $R^1$. Examples of the optionally substituted alkyl and lower alkoxy groups are as described about $R^2$ and $R^3$.

Particular examples of compounds represented by the general formula [1] are as follows. The number described corresponds to the compound number.

1) 1-[(2'-Carboxybiphenyl-4-yl)methyl]-2-n-butyl-1H-naphthimidazol-4,9-dione,
2) 1-[(2'-t-Butoxycarbonylbiphenyl-4-yl)methyl]-2-n-butyl-1H-naphthimidazol-4,9-dione,
3) 1-[(2'-(Tetrazole-5-yl)biphenyl-4-yl)methyl]-2-n-butyl-1H-naphthimidazol- 4,9-dione,
4) 1-[(2'-Carboxybiphenyl-4-yl)methyl]-2-(1-propen-1-yl)-1H-naphthimidazol- 4,9-dione,
5) 1-[(2'-(Tetrazol-5-yl)biphenyl-4-yl)methyl]-2-(1-propen- 1-yl)-1H-naphthimidazol-4,9-dione,
6) 1-[(2'-Carboxybiphenyl-4-yl)methyl]-2-(1-propyn-1-yl )- 1H-naphthimidazol-4,9-dione,
7) 1-[(2'-(Tetrazol-5-yl)biphenyl-4-yl)methyl]-2-(1-propyn-1-yl)- 1H-naphthimidazol-4,9-dione,
8) 1-[(2'-Carboxybiphenyl-4-yl)methyl]-2-phenyl-1H-naphthimidazol-4,9-dione,
9) 1-[(2'-(Tetrazol-5-yl)biphenyl-4-yl)methyl]-2-phenyl-1H-naphthimidazol-4,9-dione,
10) 1-[(2'-Carboxybiphenyl-4-yl)methyl]-2-benzyl-1H-naphthimidazol-4,9-dione,
11) 1-[(2'-(Tetrazol-5-yl)biphenyl-4-yl)methyl]-2-benzyl-1H-naphthimidazol- 4,9-dione,
12) 1-[(2'-Carboxybiphenyl-4-yl)methyl]-2-trifluoromethyl-1H-naphthimidazol-4,9-dione
13) 1-[(2'-(Tetrazol-5-yl)biphenyl-4-yl )methyl]-2-trifluoromethyl- 1H-naphthimidazol-4,9-dione,
14) 1-[(2'-Carboxybiphenyl-4-yl)methyl]-2-methyl-1H-naphthimidazol-4,9-dione,
15) 1-[(2'-(Tetrazol-5-yl)biphenyl-4-yl)methyl]-2-methyl-1H-naphthimidazol- 4,9-dione,
16) 1-[(2'-Carboxybiphenyl-4-yl)methyl]-2-ethyl-1H-naphthimidazol-4,9-dione,
17) 1-[(2'-(Tetrazol-5-yl)biphenyl-4-yl)methyl]-2-ethyl-1H-naphthimidazol-4,9-dione,
18) 1-[(2'-Carboxybiphenyl-4-yl)methyl]-2-n-propyl-1H-naphthimidazol-4,9-dione,
19) 1-[(2'-(Tetrazol-5-yl)biphenyl-4-yl)methyl]-2-n-propyl- 1H-naphthimidazol-4,9-dione,
20) 1-[(2'-Carboxybiphenyl-4-yl)methyl]-2-n-pentyl-1H-naphthimidazol- 4,9-dione
21) 1-[(2'-(Tetrazol-5-yl)biphenyl-4-yl)methyl]-2-n-pentyl-1H-naphthimidazol- 4,9-dione,
22) 1-[(2'-(Tetrazol-5-yl)biphenyl-4-yl)methyl]-2-n-hexyl-1H-naphthimidazol-4,9-dione,
23) 1-[(2'-Carboxybiphenyl-4-yl)methyl]-2-n-butyl-5,8-dimethoxy- 1H-naphthimidazol-4,9-dione,
24) 1-[(2'-Tetrazol-5-yl)biphenyl-4-yl)methyl]-2-n-butyl-6,7-dimethyl- 1H-naphthimidazol-4,9-dione,
25) 1-[(2'-Carboxybiphenyl-4-yl)methyl]-2-n-butyl-1H-benzimidazol-4,7-dione,
26) 1-[(2'-Carboxybiphenyl-4-yl)methyl]-2-n-butyl-5,6-dimethyl-1H-benzimidazol-4,7-dione,
27) 1-[(2'-(Tetrazol-5-yl)biphenyl-4-yl)methyl]-2-n-butyl-5,6-dimethyl- 1H-benzimidazol-4,7-dione,
28) 1-[(2'-Carboxybiphenyl-4-yl)methyl]-2-n-butyl-5,6-dimethoxy-1 H-benzimidazol-4,7-dione,
29) 1-[(2'-(Tetrazol-5-yl)biphenyl-4-yl)methyl]-2-n-butyl- 5,6-dimethoxy-1H-benzimidazol-4,7-dione,
30) 1-[(2'-Carboxybiphenyl-4-yl)methyl]-2-n-butyl-5,6-dihydroxymethyl- 1H-benzimidazol-4,7-dione,
31) 1-[(2'-(Tetrazol-5-yl)biphenyl-4-yl)methyl]-2-n-butyl-5,6-dihydroxymethyl- 1H-benzimidazol-4,7-dione,
32) 1-[(2'-Carboxybiphenyl-4-yl)methyl]-2-n-butyl-5-methyl-6-carboxymethyl- 1H-benzimidazol-4,7-dione,
33) 1-[(2'-(Tetrazol-5-yl)biphenyl-4-yl)methyl]-2-n-butyl-5-methyl- 6-carboxymethyl-1H-benzimidazol-4,7-dione,
34) 1-[(2'-Carboxybiphenyl-4-yl)methyl]-2-n-butyl-5-carboxymethyl-6-methyl- 1H-benzirnidazol-4,7-dione,
35) 1-[(2'-(Tetrazol-5-yl)biphenyl-4-yl)methyl]-2-n-butyl-5-carboxymethyl- 6-methyl-1H-benzimidazol-4,7-dione,
36) 1-[(2'-Carboxybiphenyl-4-yl)methyl]-2-n-butyl-5-methyl-6-carboxy- 1H-benzimidazol-4,7-dione,
37) 1-[(2'-(Tetrazol-5-yl)biphenyl-4-yl)methyl]-2-n-butyl-5-methyl-6-carboxy- 1H-benzimidazol-4,7-dione,
38) 1-[(2'-Carboxybiphenyl-4-yl)methyl]-2-n-butyl-5-carboxy- 6-methyl-1H-benzimidazol-4,7-dione,
39) 1-[(2'-(Tetrazol-5-yl)biphenyl-4-yl)methyl]-2-n-butyl-5-carboxy-6-methyl- 1H-benzimidazol-4,7-dione,
40) 1-[(2'-Carboxybiphenyl-4-yl)methyl]-2-n-butyl-5-methyl- 6-(N,N-dimethyl)carbamoyl-1H-benzimidazol-4,7-dione,
41) 1-[(2'-(Tetrazol-5-yl)biphenyl-4-yl)methyl]-2-n-butyl-5-methyl- 6-(N,N-dimethyl)carbamoyl-1H-benzirmidazol-4,7-dione,
42) 1-[(2'-Carboxybiphenyl-4-yl)methyl]-2-n-butyl-5-(N,N-dimethyl)carbamoyl- 6-methyl-1H-benzimidazol 4,7-dione,
43) 1-[(2'-Tetrazol-5-yl)biphenyl-4-yl)methyl]-2-n-butyl-5-(N,N-dimethyl)carbamoyl-6-methyl-1H-benzimidazol-4,7-dione,
44) 1-[(2'-Carboxybiphenyl-4-yl)methyl]-2-n-butyl-5-methyl-6-cyano- 1H-benzimidazol-4,7-dione,
45) 1-[(2'-(Tetrazol-5-yl)biphenyl-4-yl)methyl]-2-n-butyl-5-methyl- 6-cyano-1H-benzimidazol-4,7-dione,
46) 1-[(2'-Carboxybiphenyl-4-yl)methyl]-2-n-butyl-5-cyano- 6-methyl-1H-benzimidazol-4,7-dione,
47) 1-[(2'-(Tetrazol-5-yl)biphenyl-4-yl)methyl]-2-n-butyl-5-cyano- 6-methyl-1H-benzimidazol-4,7-dione,
48) 1-[(2'-Carboxybiphenyl-1,4-yl)methyl]-2-n-butyl-5, 6-dicyano-1H-benzimidazol-4,7-dione,
49) 1-[(2'-(Tetrazol-5-yl)biphenyl-4-yl)methyl]-2-n-butyl-5,6-dicyano- 1H-benzimidazol-4,7-dione,
50) 1-[(2'-Carboxybiphenyl-4-yl)methyl]-2-n-butyl-5-methyl- 6-(N-methanesulfonyl)carbamoyl-1H-benzimidazol-4,7-dione,
51) 1-[(2'-(Tetrazol-5-yl)biphenyl-4-yl)methyl]-2-n-butyl-5-methyl- 6-(N-methanesulfonyl)carbamoyl-1H-benzimidazol-4,7-dione,
52) 1-[(2'-Carboxybiphenyl-4-yl)methyl]-2-n-butyl-5-methyl-6-(2-carboxy)ethyl- 1H-benzimidazol-4,7-dione,
53) 1-[(2'-(Tetrazol-5-yl)biphenyl-4-yl)methyl]-2-n-butyl-5-methyl-6-( 2-carboxy)ethyl-1H-benzimidazol-4, 7-dione,
54) 1-[(2'-Carboxybiphenyl-4-yl)methyl]-2-n-butyl-5-methyl-6-( 3-carboxy)propyl-1H-benzimidazol4,7-dione,
55) 1-[(2'-(Tetrazol-5-yl)biphenyl-4-yl)methyl]-2-n-butyl-5-methyl-6-( 3carboxy)propyl-1H-benzimidazol-4, 7-dione,
56) 1-[(2'-Carboxybiphenyl-4-yl)methyl]-2-n-butyl-5-methyl-6-(4-carboxy)butyl-1H-benzimidazol-4,7-dione, 57) 1-[(2'-(Tetrazol-5-yl)biphenyl-4-yl)methyl]-2-n-butyl-5-methyl-6-( 4-carboxy)butyl-1H-benzimidazol-4,7-dione,
58) 1-[(2'-Carboxybiphenyl-4-yl)methyl]-2-n-butyl-5-methyl-6-( 2-hydroxyethyl)-1H-benzimidazol-4,7-dione,
59) 1-[(2'-(Tetrazol-5-yl)biphenyl-4-yl)methyl]-2-n-butyl-5-methyl-6-( 2-hydroxyethyl)-1H-benzimidazol-4,7-dione,
60) 1-[(2'-Carboxybiphenyl-4-yl)methyl]-2-n-butyl-5-methyl-6-( 3-hydroxypropyl)-1H-benzimidazol-4,7-dione,
61) 1-[(2'-(Tetrazol-5-yl)biphenyl-4-yl)methyl]-2-n-butyl-5-methyl-6-( 3-hydroxypropyl)-1H-benzimidazol-4,7-dione,
62) 1-[(2'-Carboxybiphenyl-4-yl)methyl]-2-n-butyl-5-methyl-6-(4-hydroxybutyl)- 1H-benzimidazol-4,7-dione,
63) 1-[(2'-(Tetrazol-5-yl)biphenyl-4-yl)methyl]-2-n-butyl-5-methyl-6-( 4-hydroxybutyl)-1H-benzimidazol-4,7-dione,
64) 1-[(2'-(Tetrazol-5-yl)biphenyl-4-yl)methyl]-1H-naphthimidazol-4,9-dione,
65) 1-[(2'-(N-Methanesulfonyl)carbamoylbiphenyl-4-yl)methyl]-2-n-butyl- 1H-naphthimidazol-4,9-dione
66) 1-[(2'-(Tetrazol-5-yl)biphenyl-4-yl)methyl]-2-ethyl-5,6-dimethyl- 1H-benzimidazol-4,7-dione,
67) 1-[(2'-(Tetrazol-5-yl)biphenyl-4-yl)methyl]-2-n-propyl-5,6-dimethyl- 1H-benzimidazol-4,7-dione,
68) 1-[(2'-(Tetrazol-5-yl)biphenyl-4-yl)methyl]-2-n-pentyl- 5,6-dimethyl-1H-benzimidazol-4,7-dione,
69) 1-[(2'-(Tetrazol-5-yl)biphenyl-4-yl)methyl]-2-n-hexyl- 5,6-dimethyl-1H-benzimidazol-4,7-dione,
70) 1-[(2'-(Tetrazol-5-yl)biphenyl-4-yl)methyl]-4-methoxyimino- 2-n-propyl-1H-naphthimidazol-9-one,
71) 1-[(2'-(Tetrazol-5-yl)biphenyl-4-yl)methyl]-2-n-butyl- 4-methoxyimino-1H-naphthimidazol-9-one,
72) 1-[(2'-(Tetrazol-5-yl)biphenyl-4-yl)methyl]-5,6-dimethyl-4-methoxyimino- 2-n-propyl-1H-benzimidazol-7-one,
73) 1-[(2'-(Tetrazol-5-yl)biphenyl-4-yl)methyl]-2-n-butyl-5,6-dimethyl- 4-methoxyimino-1H-benzimidazol-7-one.

Additional compounds of this invention include:
74) 1-[(2'-(Tetrazol-5-yl)biphenyl-4-yl)methyl]-2-n-butyl- 4-ethylidene-1H-naphtimidazol-9-one,
75) 1-[(2'-(Tetrazol-5-yl)biphenyl-4-yl)methyl]-2-n-butyl- 4-benzylidene-1H-naphtimidazol-9-one,
76) 1-[(2'-(Tetrazol-5-yl)biphenyl-4-yl)methyl]-2-n-butyl-4-( 2,2-dimethyl)propylidene-1H-naphtimidazol-9-one,
77) 1-[(2'-(Tetrazol-5-yl)biphenyl-4-yl)methyl]-2-n-butyl- 4-ethylidene-5,6-dimethyl-1H-benzimidazol-7-one,
78) 1-[(2'-(Tetrazol-5-yl)biphenyl-4-yl)methyl]-2-n-butyl-4-benzylidene- 5-methyl-6-(2-carboxy)ethyl-1H-benzimidazol-7-one,
79) 1-[(2'-(Tetrazol-5-yl)biphenyl-4-yl)methyl]-2-n-butyl-4-( 2,2-dimethyl)propylidene-5-methyl-6-(2-hydroxy)ethyl-1H-benzimidazol-7-one,
80) 1-[(2'-(Tetrazol-5-yl)biphenyl-4-yl)methyl]-2-n-butyl-1H-naphtimidazol-4,9-dione methylhydrazone,
81) 1-[(2'-(Tetrazol-5-yl)biphenyl-4-yl)methyl]-2-n-butyl-5,6-dimethyl- 1H-benzimidazol-4,7-dione phenylhydrazone.

The imidazobenzoquinones of the present invention can form a pharmacologically acceptable ester at a pan of $R^2$, $R^3$ or Y in the general formula [1], or at a pan of $X^1$ or $X^2$ in the general formulas [1a–d]. As examples of the formed esters, there are methoxycarbonyl, ethoxycarbonyl, n-propoxycarbonyl, isopropoxycarbonyl, n-butoxycarbonyl or t-butoxycarbonyl.

Further, imidazobenzoquinones of the present invention can form a pharmacologically acceptable salt at a pan of imidazole in the general formula [1] when Y is —$CO_2R^4$, —CONR'R". As examples of such a salt, there are hydrochloride, hydrobromide, hydroiodide, sulphate, phosphate, acetate, propionate, lactate, maleate, malate, succinate, tartrate and the like. And when Y is the 1H-tetrazol-5-yl in the general formula [1], they can form an alkali metal salt at a part of the 1H—. In both of cases, these salts may be in the form of a hydrate.

Imidazobenzoquinones represented by the general formula [1] can be prepared, for example, according to the following scheme.

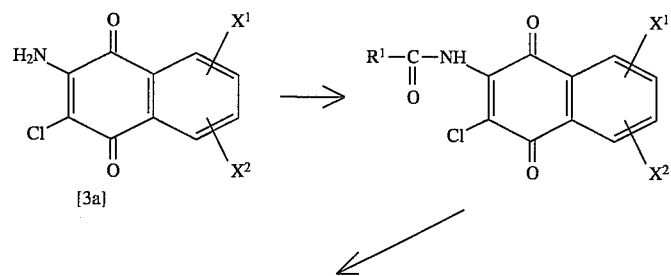

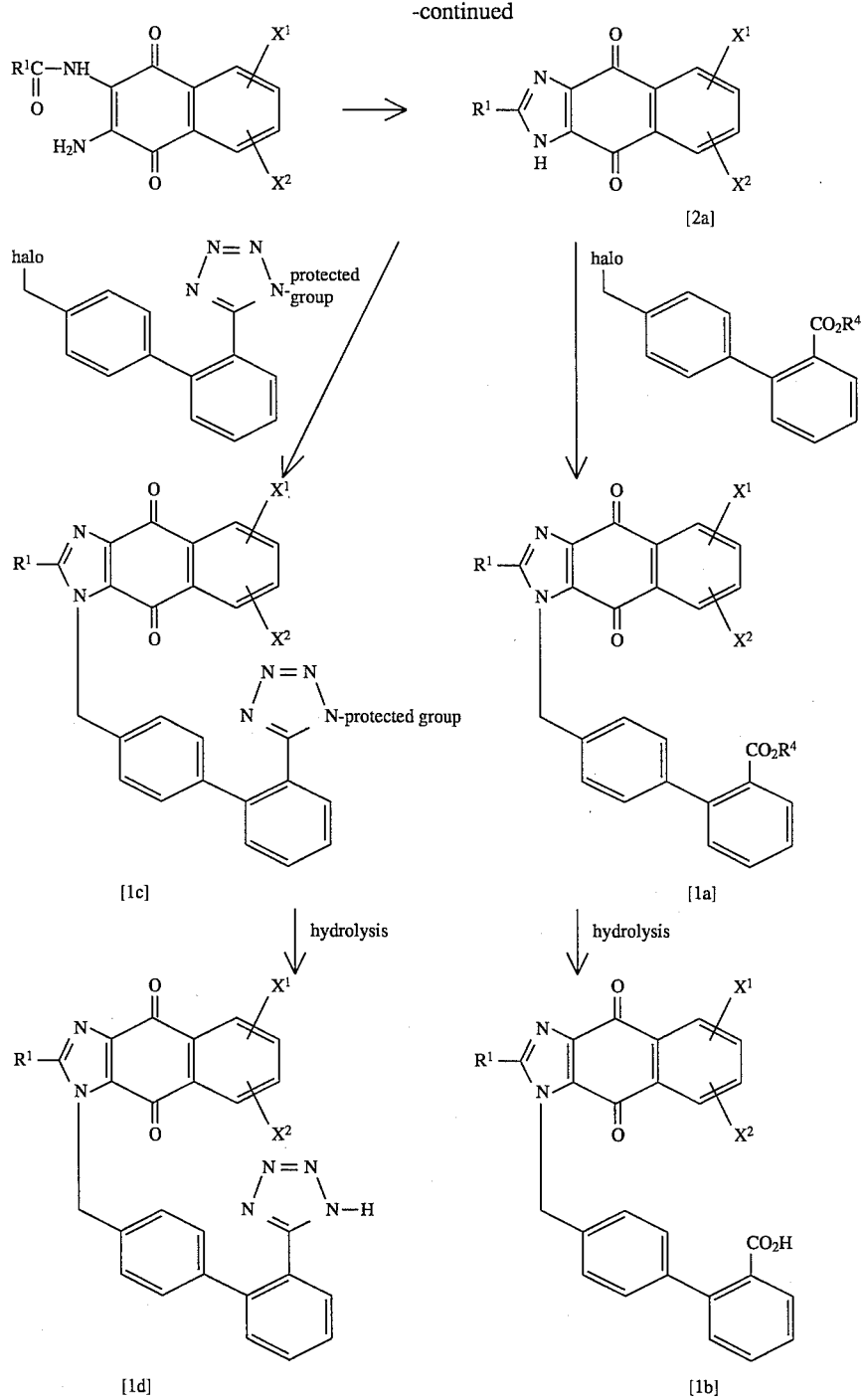

wherein $X^1$ and $X^2$ are a hydrogen atom, a halogen atom, a lower alkyl group, —$CF_3$, a lower alkoxy group, —CN, —$CO_2R^4$, a —CONR'R" group, a —$CONHSO_2R^5$ group, a —$SO_3H$ group or an alkali metal salt thereof, or a —$SO_2NHR^5$ group, and $R^4$, R', R" and $R^5$ are as defined above.

The compound [2a] which is used in this process is synthesized according to the method reported by J. R. E. Hoover, A. R. Daty in J. Am. Chem. Soc., 76, 4151 (1954).

That is, after 2-amino-3-chloro-1,4-naphthoquinone [3a] is subjected to the conventional acylation reaction, a chloro atom is converted into an amino group by treating with ammmmonia gas at about 150° C., and further an intramolecular cyclization reaction is carried under the basic condition to obtain the compound [2a] at high yield.

An alternative process is as follows:

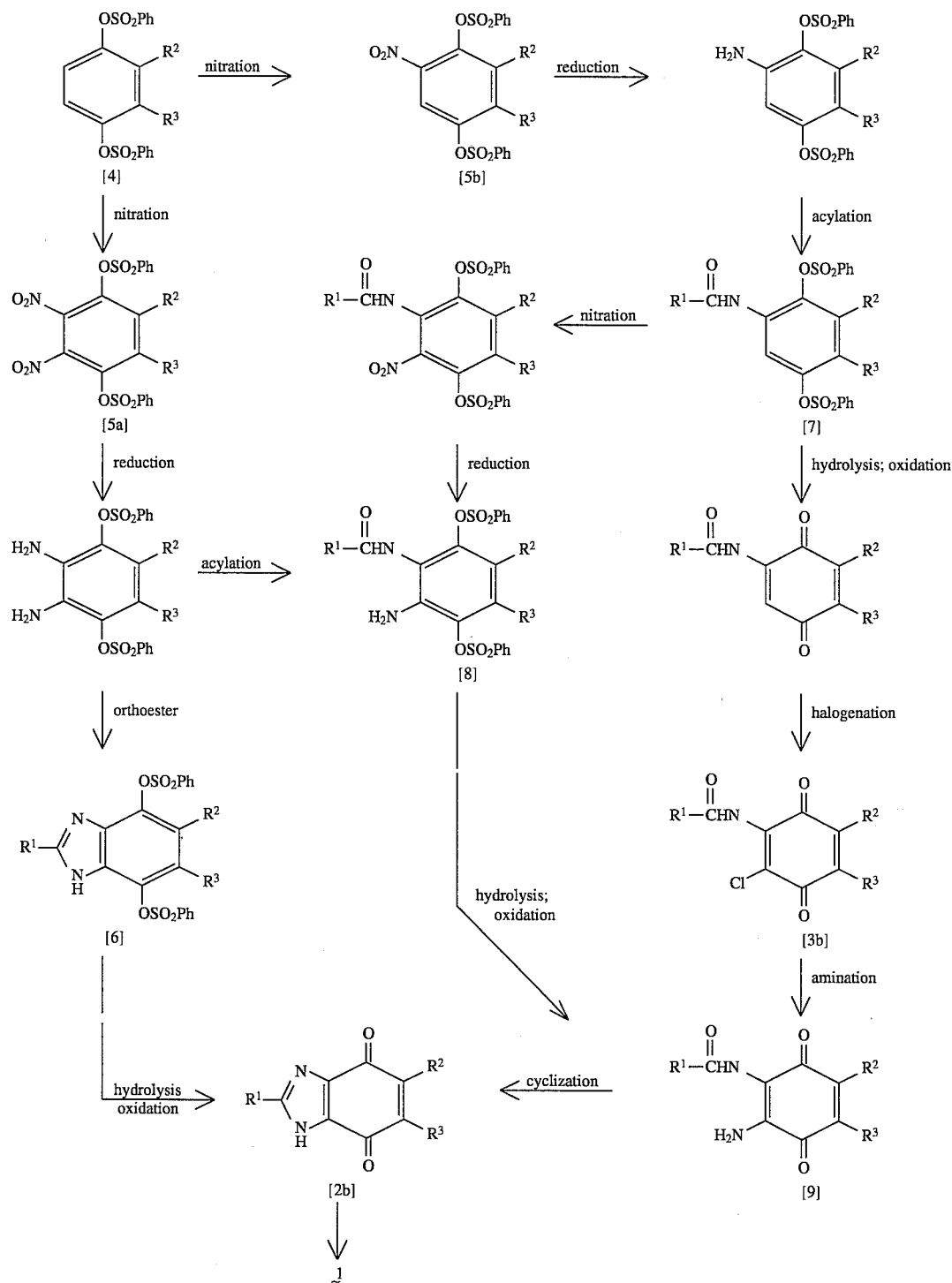

That is, in this process, the compound [4] obtained by reacting a hydroquinone derivative and benzenesulfonyl chloride according to the process by E. M. Kampouris (J. Chem. Soc. (c), 1967, 1235) is used as a starting material. Benzyl chloride can be used as a protecting group for phenols instead of benzenesulfonyl chloride. However, a desirable protecting group must be selected in view of subsequent reactions and the like. That is, when benzenesulfonyl chloride is used, the protecting group is easily cleaved under alkaline conditions, and when benzyl chloride is used, the protecting group is easily cleaved under reductive conditions, while it is stable under alkaline conditions. As a representative example, the use of benzenesulfonyl chloride will be described below. The compound [4] can be converted into the dinitro [5a] and/or mononitro [5b] compounds by reacting with fuming nitric acid according to the above-described method. The compound [5a] can be converted into a corresponding diamine by reduction using sodium dithionite, conventional catalytic reduction or reduction using a metal, for example, zinc-acetic acid, zincpotassium chloride-ethanol/water. The diamine can be convened into the compound [6] according to the reaction by heating with an orthoester which is widely known as the imidazole synthesizing method. The compound [7] can be converted into the imidazoquinone [2b] by subjecting a conventional hydrolysis reaction into a corresponding hydroquinone with an alcoholic solution of sodium or potassium hydroxide, then subjecting to the oxidation reaction.

On the other hand, the above-described mononitro compound [5b] can be similarly converted into the compound [7] by reduction reaction and acylating reaction. The compound [7] can be convened into compound [8] using again nitration reaction and reduction reaction. Alternatively, the compound [8] can be synthesized also by acylating a diamine obtained by reducing the compound [Sa]. The compound [8] can be converted into the diarainoquinone [9] by subjecting to hydrolysis reaction and then oxidation reaction, and the compound [9] can be fused into an imidazole ring according to the method by J. R. E. Hoover described above. Also, the compound [7] itself can be converted into the compound [3b] by halogenation reaction after hydrolysis and oxidation reaction into a monoaminoquinone. The synthesis of the imidazoquinone [2b] from the compound [3b] via the compound [9] may be carried out according to the method by J. R. E. Hoover.

Imidazobenzoquinones in the general formula [1] wherein X is oxygen atom can be derived into a monooxime, for example, by heating with a hydrochloride of hydroxylamine, alkoxyamine and the like in pyridine.

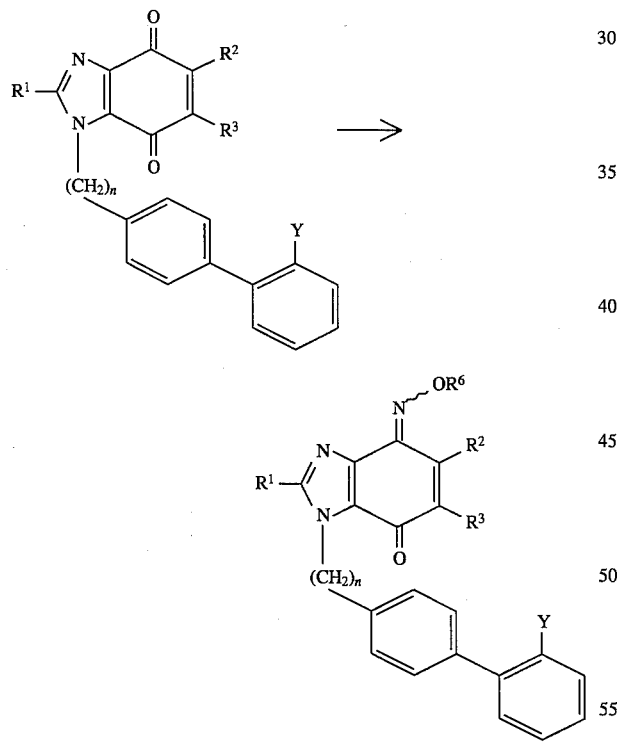

The conversion of the diketone to compounds wherein X is N—NHR$^5$ or CR$^7$R$^8$ is similarly undertaken using procedures well known in the art, analogous to those described herein.

Pharmacological activity test of the compound of the present invention is described hereinafter.

1) In vitro angiotensin II mesenteric artery receptor binding assay

According to the method (1) by Gunther et at., a membrane fraction was prepared from mesenteric artery of a male rat, 50 μg protein equivalent thereof and 0.2 nM $^{125}$I-Ang II as well as various concentrations of test compounds were incubated at 22° C. for 90 min. in 200 μl reaction volume of incubation buffer (50 mM Tris-HCl, 120 mM NaCl, 5 mM MgCl$_2$, 0.25% bovine serum albumin, pH7.2). This was cooled, and the reaction was stopped by addition of ice-cooled phosphate buffer (10 mM phosphate, 140 mM NaCl, pH7.4, hereinafter referred to as PBS), and then the reaction solution was filtered through a glass fiber filter (Whatman CF/B), the filter was washed, dried, and then the radioactivity of captured $^{125}$I-angiotensin II which bound to the receptor was measured by γ-counter. Non-specific binding mount was obtained from the reaction in the presence of 1 μM of unlabeled angiotensin II. The test compound was tested at the concentration of 0.01 to 1 μM, and those that inhibited more than 50% of total specific binding mount at 1 μM was determined as an active compound, and 50% inhibiting concentration (IC$_{50}$) was obtained [see Gunther, S., Gimbrone, M. A. and Alexander, R. W., Circ. Res., 17:278–286, 1980].

2) In vitro adrenal cortex angiotensin II receptor binding assay

According to the method by Capponi et at. (1), angiotensin II receptor binding assay was carried out by preparing a membrane fraction from an adrenal cortex of a male rat and using this as a receptor material in the same manner as in the above-described pharmacological test 1) [see Capponi, A. M. and Catt, K., J. Biol. Chem. 254:5120–5127(1979)].

3) Antagonism to angiotensin II constriction in an isolated rabbit thoracic aorta A rectangular strip-like sample of thoracic aorta isolated from an anethetized rabbit was prepared, and this was suspended at 2.0 g of loaded tension in a Magnus tube filled with Krebs-Henseleitoid nutrition solution which was well aerated with 95% O$_2$-5% CO$_2$, and the constriction tension was measured using an isometric transducer. After the tension of the sample at rest became stable, accumulative administration of angiotensin II was carried out to obtain a concentration-action curve. Thereafter, the sample was washed with the same nutrition solution, and then 10$^{-6}$M test compound was treated for 20 min. to obtain again a concentration-action curve of angiotertsin II. The results were obtained as followed: generated maximum tension at the first accumulative administration of angiotensin II was regarded as 100%, and the 50% effective concentration (ED$_{50}$) was obtained in the presence or absence of the test compound, and pA$_2$ value was calculated according to the following equations:

$$pA_2 = -\log K_B K_B = C/\{(A'/A)-1\}$$

C: concentration of the test compound (M)

A': ED$_{50}$ in the presence of test compound (M)

A: ED$_{50}$ in the absence of the test compound (M)

4) Antagonism to blood pressure increasing by angiotensin II in a spine destroyed rat Wistar rat anesthetized with pentobarbital was fixed at dorsal position, and a cannula for measuring blood pressure was inserted into sinister arteria carotis communis, and a cannula for administration of the test compound into dexter external jugular vein and a cannula for administration of angiotensin II into sinister external jugular vein, arebilateral nervous vagus was cut, and artificial respiration was carried out. A thin bar made of metal was stabbed into spinal column through sininster orbita to destroy spine. Blood pressure was recorded on polygraph via pressure transducer from an arterial cannula. After blood pressure was stable for more than 30 min., 3μg/kg of angiotensin II was administered intravenously four times every 15 min., and every 5 min. before the administration of angiotensin II from the second admininstration onward, a solvent, a lower dose of the test compound, and a higher dose of the test compound were admininstered intravenously in this order to observe the blood pressure increasing response by angiotensin II. $ED_{50}$ values were calculated from the inhibiting rate when the first blood pressure increase by angiotensin II was regarded as 100%.

In above tests, the compounds of the present invention showed high activity. For example, the compound No. 1 and No. 2 showed $IC_{50}=6.1\times10^{-7}M$ or $5.0\times10^{-8}M$ in the test 1), respectively. And the compound No. 1 showed $IC_{50}=5.4\times10^{-7}M$, $pA_2=6.64$, and the compound No. 2 showed $IC_{50}=4.8\times10^{-8}M$, $pA_2=7.60$ in tests 2) and 3), respectively. Further, the compound No. 1 showed $ED_{50}$ value=22.6 mg/kg in the test 4).

The imidazobenzoquinones or pharmacologically acceptable esters or salts thereof can be formulated, by a conventional method, into a dosage unit forms such as tablets, capsules, pills, powders, granules, powder packet, cachets, sterile parenteral solutions or suspensions, eyedrops, solutions or suspensions, elixirs, suppositories, aerosols and emulsions which contains them in a predetermined amount.

For oral admininstration, solid or fluid unit dosage form can be prepared. For preparing solid composition, the active compound is mixed with an excipient or a carrier such as magnesium stearate, dicalcium phosphate, magnesium aluminum silicate, calcium sulphate, starch, lactose, acacia, methyl cellulose and the like. A capsule agent is prepared by mixing the compound of the present invention with an inert pharmaceutical excipient, filling the mixture into a hard gelatin capsule having suitable size. A soft gelatin capsule is prepared by machine capsulation of slurry composed of the compound, suitable vegetable oil, light petrolatum or other inert oil.

For preparing a fluid composition, the compound of the present invention is dissolved in aqueous vehicle together with sugar, aromatic flavor and preservative to obtain a syrup. Elixirs are prepared using an alcoholic vehicle such as ethanol, a sweetener such as sugar and saccharin as well as a flavor. Suspensions are prepared using a suspending agent such as acacia, tragacanth or methyl cellulose and an aqueous vehicle.

For parenteral administration, a fluid unit dosage form is prepared using the compound of the present invention and a sterile vehicle. Depending upon a vehicle such as water, Ringer's solution, isotonic sodium chloride solution and the concentration to be used, the compound is suspended or dissolved in the vehicle. For preparing solutions, the compound is dissolved in water for injection, and this is sterile filtered, filled into a vial or an ampoule, and sealed. Advantageously, an adjuvant such as local anesthetic, preservative and buffer is dissolved in vehicle. Alternatively, a lyophilized powder having good shelf stability can be prepared. In the case of this formulation, the powder is reconstituted upon use. Parenteral suspensions can be similarly prepared using the compound of the present invention. In the case of this formulation, the compound of the present invention can be sterilized by exposure to ethylene oxide before suspended in a sterile vehicle. Advantageously, a surfactant or a wetting agent is added to facilitate dispersion of the compound.

Alternatively, the compound of the present invention can be formulated into a local dosage form in combination with a suitable carrier for local administration. Examples of a carrier to be used are cream, ointment, lotion, paste, jelly, spray, aerosol and the like. Further, when other form can not be administered, suppositories can be prepared. Examples of a base are cacao butter, polyethylene glycol, polyethylene sorbitan monostearate and the like.

Imidazobenzoquinones or pharmacologically acceptable esters or salts thereof are administered orally, parenterally by insufflation, rectally, locally. Parenteral administration includes subcutaneous, intravenous, intramuscular, intranasal adminstration or injection. Dose to be administered to an adult is in a range of 1 to 50 mg/day. The exact dose can be selected the above range, taking into account the age of patient, weight, condition and route of administration into consideration. Frequency of administration is usually one to four times a day.

Additionally, no toxicity of the compound of the present invention or pharmacologically acceptable esters or salts thereof was observed in the above-described dose range.

DETAILED DESCRIPTION OF THE INVENTION

The following Examples further illustrate the present invention in detail but are not to be construed to limit the scope thereof.

EXAMPLE 1

Preparation of 1-[(2'-carboxybiphenyl-4-yl)methyl]-2-n-butyl-1H-naphthimidazol-4,9-dione (Compound No. 1)

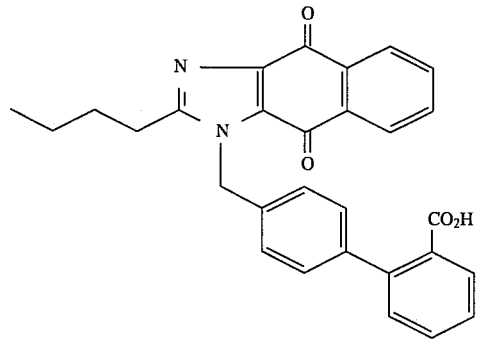

73 mg (0.29 mmol) of 2-n-Butyl-1H-naphthimidazol-4, 9-dione which had been synthesized according to the known method in the reference [J. Am. Chem. Soc., 76, 4151(1954)] was dissolved in 3 ml of dimethylformamide. After 0.35 mmol of sodium hydride was added at 15° to 20° C. under the nitrogen atmosphere, 100 mg (0.29 mmol) of (2'-t-butoxycarbonylbiphenyl-4-yl)methyl bromide was added to react for 2.5 hours. The reaction mixture was poured into water, and the mixture was extracted with ethyl acetate, washed with water and dried with magnesium sulphate. The solvent was distilled off under the reduced pressure, the residue was purified by silica gel column chromatography ($CHCl_3$:MeOH=30:1) to obtain 99 mg of 1-[(2'-t-butoxycarbonylbiphenyl-4-yl)methyl]-2-n-butyl-1H-naphthimidazol-4,9-dione (Compound No. 2). NMR spectrum is as follows. δ ppm ($CDCl_3$): 1.00 (3H, t, J=7 Hz), 1.26 (9H, s), 1.49 (2H, sextet, J= 7 Hz), 1.91 (2H, quintet, J=8 Hz), 2.88 (2H, t, J=8 Hz), 5.83 (2H, s), 7.22 (2H, d, J=8 Hz), 7.31–7.37 (3H, m), 7.45 (1H, ddd, J=8, 8.2 Hz), 7.53 (1H, ddd, J=8, 8.2 Hz), 7.72–7.85 (3H, m), 8.14–8.20 (1H, m), 8.29–8.35 (1H, m)

99 mg of the compound was reacted at reflux for 3 hours under the nitrogen atmosphere in trifluoroacetic acid (2 ml)-chloroform (2 ml) solution. The solvent was distilled off under the reduced pressure, the residue was poured into water, extracted with methylene chloride, washed with a solution of sodium bicarbonate, dried with sodium sulphate. The solvent was distilled off under the reduced pressure, the residue was purified by silica gel column chromatography (developing solvent: CHCl$_3$/MeOH=30/1) to obtain 65 mg of 1-[( 2'-carboxybiphenyl-4-yl)methyl]-2-n-butyl-1H-naphthimidazol-4,9-dione (Compound No. 1: U-93211), as pale yellow crystal. This has the following NMR spectrum. δ ppm (CDCl$_3$): 0.90 (3H, t, J=7 Hz), 1.39 (2H, sextet, J=7 Hz), 1.77 ( 2H, quintet, J=8 Hz), 2.84 (2H, t, J=8 Hz), 5.81 (2H, s), 7.23 (2H, d, J=8 Hz), 7.40–7.33 ( 3H, m), 7.48 (1H, ddd, J=8, 8.1 Hz), 7.60 (1H, ddd, J=8, 8.1 Hz), 7.69–7.79 (2H, m), 8.01 (1H, dd, J= 8.13–8.17 (1H, m), 8.25–8.29 (1H, m)

EXAMPLE 2

Preparation of 1-[(2'-(tetrazol-5-yl)biphenyl-4-yl)methyl]-2-n-butyl-1H-naphthimidazol-4,9-dione (Compound No. 3)

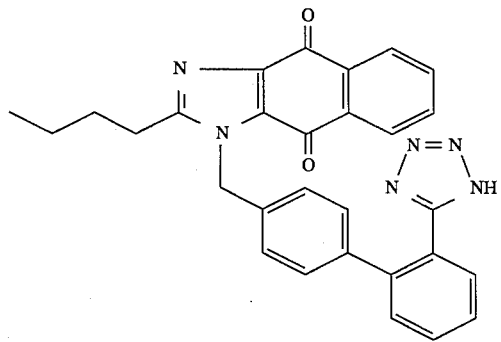

According to the same manner as that described in Example 1, 122 mg (0.5 mmol) of 2-n-butyl-1H-naphthimidazol-4,9-dione and 0.58 mmol of sodium hydride were reacted in 3 ml of dimethylformamide under the nitrogen atmosphere, then 287 mg (0.5 mmol) of (2'-( 1-triphenylmehtyltetrazol-5-yl)biphenyl-4-yl)methyl bromide was reacted. After the reaction, the similar treatment was carried out, and purified by silica gel column chromatography to obtain 160 mg of 1-[(2'-(1-triphenylmethyltetrazol-5-yl)biphenyl-4-yl)methyl]- 2-n-butyl-1H-naphthimidazol-4,9-dione. This has the following NMR spectrum. δ ppm (CDCl$_3$): 0.88 (3H, t, J=7 Hz), 1.33 (2H, sextet, J=8 Hz), 1.75 ( 2H, quintet, J=8 Hz), 2.66 (2H, t, J=8 Hz), 5.61 (2H, s), 6.89–6.93 (8H, m), 7.11 (2H, d, J=8 Hz), 7.21–7.34 (10H, m), 7.41–7.51 (2H, m), 7.65–7.76 (2H, m), 7.89–7.94 (1H, m), 8.25–8.28 (1H, m)

160 mg of the compound was reacted at room temperature for 5 hours in 10% aqueous hydrochloride (0.3 ml)-acetone (3 ml), then the mixture was extracted with chloroform, washed with sodium bicarbonate, and dried with sodium sulphate. The solvent was distilled off under the reduced pressure, the residue was purified by silica gel column chromatography (developing solvent: CHCl$_3$/MeOH:30/1-10/1) to obtain 98 mg of 1-[(2'-(tetrazol-5-yl)biphenyl-4-yl)methyl]-2-n-butyl-1H-naphthimidazol-4,9-dione (Compound No. 3: U-93285) as pale yellow crystals. This has the following NMR spectrum. β ppm (CDCl$_3$): 0.80 (3H, t, J=7 Hz), 1.29 (2H, sextet, J=8 Hz), 1.61 (2H, quintet, J=8 Hz); 2.66 (2H, t, J=8 Hz), 5.62 (2H, s), 7.01–7.09 (4H, m), 7.32 (1H, dd, J= 8.2Hz), 7.41 (1H, ddd, J=8, 8.2 Hz), 7.49 (1H, ddd, J=8, 8.2 Hz), 7.61–7.67 (2H, m), 7.81 ( 1H, dd, J=8.1 Hz), 7.98–8.08 (2H, m)

EXAMPLES 3 to 11

According to the same manner as that described in Example 1, various 2-substituted 1H-naphthimidazol-4,9-diones were reacted with (2'-t-butoxycarbonylbiphenyl-4-yl)methyl bromide and then subjected to hydrolysis to obtain 2-substituted 1-[(2'-carboxybiphenyl- 4yl)methyl]-1H-naphthimidazol-4,9-diones.

Results are shown in Tables 1 and 2. All reactions were carried out by using an equivalent molar amount of (2'-t-butoxyarbonylbiphenyl-4-yl)methyl bromide relative to the compound [2a] (X$_1$=X$_2$=H) in the presence of 1.2 equivalent amount of sodium hydride.

TABLE 1

| Example | R$^1$ | Yield (%) | MS (me/e) | NMR(δppm) | Comp. No. |
|---|---|---|---|---|---|
| 3 | Me | 75.7 | 422 | DMSO-d$_6$ δ2.45(3H, s), 5.75(2H, s), 7.24–7.70(8H, m), 7.82–7.89(2H, m), 8.06–8.16(2H, m) | 14 |
| 4 | Et | 77.3 | 436 | DMSO-d$_6$ δ1.22(3H, t, J=7.5Hz), 2.77(2H, q, J=7.5Hz), 5.78(2H, s), 7.20–7.68(8H, m), 7.82–7.86(2H, m), 8.05–8.11(2H, m) | 16 |
| 5 | nPr | 71.0 | 450 | CD$_3$OD δ0.91(3H, t, J=7.5Hz), 1.70(2H, sex., J=7.5Hz), 2.74(2H, t, J=7.5Hz), 5.80(2H, s), 7.21–7.36(5H, m), 7.44(1H, t, J=7.3Hz), 7.54(1H, t, J=7.3Hz), 7.69(1H, t, J=7.8Hz), 7.81–7.88(2H, m), 8.03–8.12(2H, m) | 18 |

TABLE 2

| Example | R$^1$ | Yield (%) | MS(me/e) | NMR(δppm) | Comp. No. |
|---|---|---|---|---|---|
| 6 | nPentyl | 62.9 | 478 | DMSO-d$_6$ δ0.82(3H, t, J =7Hz), 1.21–1.28(4H, m), 1.62–1.68(2H, m), 2.76(3H, t, J =7.5Hz), | 20 |

TABLE 2-continued

| Example | $R^1$ | Yield (%) | MS(me/e) | NMR(δppm) | Comp. No. |
|---|---|---|---|---|---|
| | | | | 5.80(2H, s),<br>7.21–7.35(5H, m),<br>7.44(1H, t, J=7.6Hz),<br>7.55(1H, t, J=7.6Hz),<br>7.70(1H, d, J=8.1Hz),<br>7.83–7.88(2H, m),<br>8.04–8.12(2H, m) | |
| 7 | $CF_3$ | 63.8 | 476 | | 12 |
| 8 | phenyl (Ph) | 54.8 | 484 | | 8 |
| 9 | benzyl ($PhCH_2$) | 29.1 | 498 | DMSO-$d_6$<br>δ4.21(2H, s),<br>5.82(2H, s),<br>7.17–7.35(9H, m),<br>7.44(1H, t, J=7.6Hz),<br>7.56(1H, t, J=7.6Hz),<br>7.70(1H, d, J=7.6Hz),<br>7.81–7.88(2H, m),<br>8.03–8.12(2H, m) | 10 |
| 10 | $CH_3CH=CH-$ | 32.9 | 448 | | 4 |
| 11 | $CH_3C\equiv C-$ | 28.6 | 446 | | 6 |

EXAMPLE 12 to 16

According to the same manner as that described in Example 2, various 2-substituted naphthimidazol-4,9-diones and (2'-(1-triphenylmethyltetrazol-5-yl)biphenyl4-yl)methyl bromide were reacted and then the deprotection reaction was carried out under strong acid conditions to synthesize 2-substituted 1-[(2'-(tetrazol-5-yl)biphenyl-4-yl)methyl]-1H-naphthimidazol- 4,9-diones.

Results are shown in Table 3. All reactions were carried out by using an equivalent molar amount of (2'-(1-triphenylmethyltetrazol-5-yl)biphenyl 4-yl)methyl bromide relative to the compound [2a] ($X_1=X_2=H$) in the presence of 1.2 equivalent mole amount of sodium hydride.

EXAMPLE 17

Preparation of 1-[(2'-carboxybiphenyl-4-yl)methyl]-2-n-butyl-5,6-dimethyl- 1H-benzimidazol-4,7-dione (Compound No. 26)

TABLE 3

| Example | $R^1$ | Yield (%) | MS (me/e) | NMR(δppm) | Comp. No. |
|---|---|---|---|---|---|
| 12 | Me | 69.9 | 446 | | 15 |
| 13 | Et | 72.2 | 460 | | 17 |
| 14 | nPr | 39.7 | 474 | $CDCl_3$<br>0.99(3H, t, J=7Hz),<br>1.77–1.93(2H, sex., J=7Hz),<br>2.77(2H, t, J=7Hz),<br>5.74(2H, s),<br>7.18(2H, d, J=8Hz),<br>7.24(2H, d, J=8Hz),<br>7.39(1H, dd, J=8Hz, J=2Hz),<br>7.51–7.59(2H, m),<br>7.68–7.74(2H, m),<br>8.09–8.15(2H, m),<br>8.19–8.24(1H, m) | 19 |
| 15 | nPentyl | 17.1 | 502 | $CDCl_3$<br>0.84(3H, t, J=7Hz),<br>1.20–1.36(4H, m),<br>1.68–1.76(2H, m),<br>2.72(2H, t, J=8Hz),<br>5.68(2H, s),<br>7.10(2H, d, J=8Hz),<br>7.16(2H, d, J=8Hz),<br>7.36(1H, dd, J=7Hz, J=2Hz),<br>7.46–7.57(2H, m),<br>7.65–7.23(2H, m),<br>7.86(1H, d, J=8Hz),<br>8.04–8.09(1H, m),<br>8.14–8.17(1H, m) | 21 |
| 16 | $CF_3$ | 73.9 | 500 | | 13 |

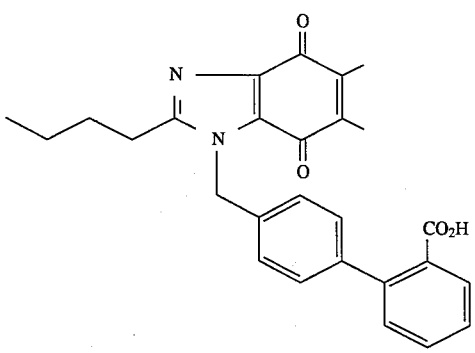

1000 mg (7.2 mmol) Of 2,3-dimethyl-p-hydroquinone was dissolved in 40 ml of acetonitrile, to this were added 6998 mg (21.5 mmol) of cesium carbonate and 2574 mg (15.1 mmol) of benzyl bromide and the mixture was heated under reflux for 3.5 hours. After the reaction solution was cooled, the precipitate was filtered, and the filtrate was concentrated under the reduced pressure to obtain 2257 mg of 2,3-dimethylhydroquinone bisbenzyl ether as brown solid (yield 100% ). This has the following NMR spectrum. δ ppm (CDCl$_3$): 2.24 (6H, s), 5.01 (4H, s), 6.70 (2H, s), 7.31–7.46 (10H, m)

2257 mg (7.2 mmol) Of the benzyl ether was suspended in 20 ml of acetic anhydride, and this was cooled to 0° C. After one drop of conc. sulfuric acid was added, 1.3 ml of 70% nitric acid was added dropwise, the reaction temperature was rosen to 50° C. and the reaction mixture was stirred for 22 hours. The reaction solution was cooled to 0° C., and water was added to obtain a precipitate which was filtered, and was washed with water and dried under the reduced pressure to obtain 1915 mg of 2,3-dimethyl-5,6-dinitrohydroquinone bisbenzyl ether as brown powder (yield 65% ). This has the following NMR spectrum. δ ppm (CDCl$_3$): 2.32 (6H, s), 5.00 (4H, s), 7.39–7.44 (10H, m)

1400 mg (3.4 mmol) Of the dinitro compound was suspended in 50 ml of methanol, and further a suspension of 11.9 g (68.4 mmol) of sodium dithionite in 50 ml of methanol was added and the mixture was heated under reflux for 4 hours. The reaction mixture was concentrated under the reduced pressure, ice-water was added, and a precipitate formed was filtered, and this was washed with water, and dried to obtain 815 mg of 2,3-dimethyl-5,6-diaminohydroquinone bisbenzyl ether as brown powder (yield 68%). This has the following NMR spectrum. δ ppm (CDCl$_3$): 2.18 (6H, s), 4.80 (4H, s), 7.35–7.50 (10H, m)

To 934 mg (2.7 mmol) of the diamine was added 457 mg (2.8 mmol) of trimethyl ortho-n-valerate, and the mixture was stirred for 25 min. at 100° C. Drying under the reduced pressure after the reaction gave 1100 mg of 2-n-buty-4,7-dibenzyloxy-5,6-dimethyl-1H-benzimidazole as brown solid (yield 99%). This has the following NMR spectrum. δ ppm (CDCl$_3$): 0.93 (3H, t, J=7 Hz), 1.31–1.39 (2H, mn), 1.59–1.65 (2H, m), 2.24 (6H,s), 2.72 (2H, t, J=8 Hz), 5.24 (4H, bs), 7.34–7.42 (10H, m)

1100 mg (2.6 mmol) Of the benzimidazole was dissolved in 60 ml of methanol, and 150 mg of 10% palladium-carbon was added. The mixture was stirred at room temperature for 22 hours under the atmosphere of 2.2 kg/cm$^2$ hydrogen. The reaction mixture was filtered, and the filtrate was stirred at room temperature for 30 min. under the atmospheric pressure, and concentrated under the reduced pressure to obtain 616 mg of 2-n-butyl-5,6-dimethyl- 1H-benzimidazol-4,7-dione (Compound 72) as brown solid (yield 100%). This has the following NMR spectrum. δ ppm (CDCl$_3$): 0.90 (3H, t, J=7 Hz), 1.34–1.42 (2H, m), 1.75–1.86 (2H, m), 2.07 (6H, s), 2.93 (2H, t, J=8 Hz)

340 mg (1.5 mmol) Of the benzimidazol-4,7-dione was dissolved in 15 ml of dimehtylformarnide, and this was cooled to 0° C. After 65 mg (1.6 mmol) of 60% sodium hydride was added and the mixture was stirred for 30 min. A solution of 503 mg (1.5 mmol) of (2'-t-butoxycarbonyl-biphenyl-4-yl)methyl bromide in 2 ml of dimethylformamide was added dropwise and the mixture was stirred for 1 hour. To the reaction mixture was added an aqueous saturated solution of ammonium chloride, and this was extracted with ethyl acetate. The organic layer was washed with an aqueous saturated sodium chloride solution, and this was dried over anhydrous sodium sulphate, and the solvent was distilled off under the reduced pressure. The resultant crude product was purified by silica gel chromatography (ethyl acetate: n-hexane=5:1) to obtain 421 mg of 1-[(2'-t-butoxy-carbonylbiphenyl-4-yl)methyl]-2-n-butyl-5,6-dimethyl-1H-benzimidazol-4,7-dione as yellow oily material (Yield 58%). This has the following NMR spectrum. δ ppm (CDCl$_3$): 0.91 (3H, t, J=7 Hz), 1.21 (9H, s), 1.35–1.43 (H, s), 1.76–1.82 (2H, m), 2.04 (3H, s), 2.10 (3H, s), 5.62 (2H, s), 7.10 (2H, d, J=8 Hz), 7.27–7.30 ( 3H, m), 7.39–7.42 (1H, m), 7.45–7.48 (1H, m), 7.78 (1H, dd, J=6, 1 Hz)

420 mg (0.8 mmol) Of the ester was dissolved in 20 ml of chloroform, and to this was added 4 ml of trifluoroacetic acid and the mixture was heated under reflux for 2 hours. After the reaction mixture was cooled, an aqueous saturated solution of sodium bicarbonate was added to adjust pH to 8. The organic layer was washed with an aqueous saturated saline solution and dried over anhydrous sodium sulphate, and the solvent was distilled off under the reduced pressure to obtain 370 mg of 1-[(2'-carboxybiphenyl-4-yl)methyl]-2-n-butyl- 5,6-dimethyl-1H-benzimidazol-4,7-dione (Compound No. 26) as yellow powder (yield 99% ). This has the following NMR spectrum. δ ppm (CDCl$_3$): 0.83 (3H, t, J=7 Hz), 1.27–1.35 (2H, m), 1.57–1.70 (2H, s), 2.09 (3H, s), 2.71 (2H, t, J=8 Hz), 5.61 (2H, s), 7.10 (2H, d, J=8 Hz), 7.31 (3H, d, J=8 Hz), 7.40–7.46 (1H, m), 7.55 (1H, dd, J=8, 1 Hz), 7.95 (1H, dd, J= 8, 1 Hz)

EXAMPLE 18

Preparation of 1-[(2'-(tetrazol-5-yl)biphenyl-4-yl)methyl]-2-n-butyl- 5,6-dimethyl-1H-benzimidazol-4,7-dione (Compound No. 27)

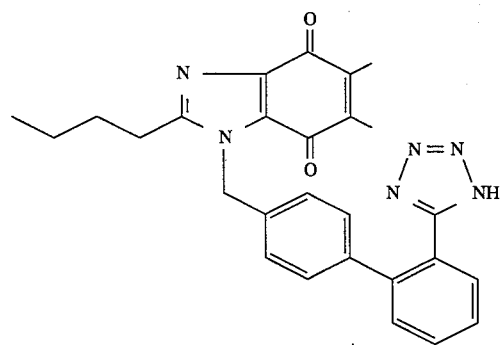

230 mg (1.0 mmol) Of 2-n-butyl-5,6-dimethyl-1H-benzimidazol-4,7-dione obtained according to the same manner as that described in Example 17 and 1.0 mmol of sodium hydride were reacted in 18 ml of dimethylformamide at 0° C. and then 552 mg (1.0 mmol) of (2'-(1-triphenylmethyltetrazol-5-yl)biphenyl-4-yl)methyl bromide was reacted. The reaction mixture was poured into water, and this was extracted with ethyl acetate, washed with water, and dried over anhydrous sodium sulphate. The solvent was distilled off under the reduced pressure, the residue was purified by silica gel chromatography (n-hexane:ethyl acetate: 10:1) to obtain 350 mg of 1-[(2'-(1-triphenylmethyltetrazol-5-yl)biphenyl-4-yl)methyl]-2-n-butyl-5,6-dimethyl-1H-benzimidazol-4,7-dione as yellow powder (yield 49%). This has the following NMR spectrum. $\delta$ ppm (CDCl$_3$): 0.86 (3H, t, J=7 Hz), 1.23–1.34 (2H, m), 1.64–1.72 ( 2H, m), 2.00 (3H, s), 2.10 (3H, s), 2.60 (2H, t, J=8 Hz), 5.47 (2H, s), 6.85 (2H, d, J=8 Hz), 6.90–6.94 (6H, m), 7.10 (2H, d, J=8 Hz), 7.22–7.36 (10H, m), 7.42–7.49 (2H, m), 7.90– 7.94 (1H, m)

350 mg (0.5 mmol) Of the benzimidazol-4,7-dione was dissolved in a mixture of 6 ml of methanol and 7 ml of acetone, and to this was added 5 ml of 2N hydrochloric acid and the mixture was stirred at 40° C. for 30 min. After the reaction mixture was cooled, this was neutralized with 2N sodium hydroxide to pH6. The reaction mixture was concentrated under the reduced pressure, and extracted with chloroform. After washed with water, this was dried over anhydrous sodium sulphate, the solvent was distilled off under the reduced pressure, and the residue was purified by silica gel chromatography (chloroform: methanol =100:1) to obtain 155 mg of 1-[(2'-(tetrazol-5-yl)biphenyl-4-yl)methyl]-2-n-butyl- 5,6-dimethyl-1H-benzimidazol-4,7-dione (Compound No. 27) as yellow powder (yield 6895). This has the following NMR spectrum. $\delta$ ppm (CDCl$_3$): 0.85 (3H, t, J=7 Hz), 1.28–1.36 (2H, m), 1.63–1.69 (2H, quintet). 2.03 (3H, s), 2.05 (3H, s), 2.65 (2H, t, J=8 Hz), 5.56 (2H, s), 7.05 (2H, d, J=8 Hz), 7.15 (2H, d, J=8 Hz), 7.37 (1H, d, J=8 Hz), 7.51–7.57 (2H, m), 7.99 (1H, d, J=8 Hz)

EXAMPLES 19 and 20

2,3-Dimethyl-5,6-diaminohydroquinone bisbenzyl ether obtained in Example 17 was reacted with various orthoester and then hydrogenated in the presence of 5% palladium-carbon catalyst. The reaction mixture was stirred in air to obtain the corresponding 2-substituted- 5,6-dimethyl-1H-benzimidazol-4,7-dione. The results are shown in Table 4.

TABLE 4

| Example | R$^1$ | Yield (%) | MS (me/e) | NMR($\delta$ppm) | Comp. No. |
|---|---|---|---|---|---|
| 19 | Et | 100 | 204 | 1.40(3H, t, J=8Hz), 2.09(6H, s), 2.91(2H, q, J=8Hz) | 66 |
| 20 | n-Pr | 100 | 218 | 0.97(3H, t, J=7Hz), 1.80–1.89(2H, m), 2.07(6H, s), 2.90(2H, t, J=7Hz) | 67 |
| 21 | n-Pent | 37 | 246 | 0.88(3H, t, J=7Hz), 1.30–1.40(4H, m), 1.78–1.83(2H, m), 2.05(6H, s), 2.87(2H, t, J=7Hz) | 68 |
| 22 | n-Hex | 39 | 260 | 0.84(3H, t, J=7Hz), 1.26–1.32(6H, m), 1.79–1.84(2H, m), 2.08(6H, s), 2.93(2H, t, J=8Hz) | 69 |

EXAMPLES 21 and 22

2,3-Dimethyl-5,6-diaminohydroquinone bisbenzyl ether obtained in Example 17 was reacted with various acid chlorides in the presence of triethylamine to obtain the corresponding monoacylated compound. The monoacylated compound was heated with phosphorous oxychloride in chloroform to obtain the corresponding 2-substituted-5,6-dimethyl- 1H-benzimidazol-4,7-bisbenzyl ether, which was hydrogenated in the presence of 5% palladium carbon. The reaction mixture was stirred in air to obtain the corresponding 2-substituted- 5,6-dimethyl-1H-benzimidazol-4,7-dione. The results are shown in Table 4.

EXAMPLE 23

Preparation of 1-[(2'-tetrazol-5-yl)biphenyl-4-yl)methyl]-2-n-butyl- 5,6-dimethyl-4-methoxyimino-1H-benzimidazol-7-one (Compound No. 73)

200 mg (0.43mmol) Of 1-[(2'-tetrazol-5-yl)biphenyl-4-yl)methyl- 2-n-butyl-5,6-dimethyl-1H-benzimidazol-4,7-dione obtained in Example 18 and 359 mg (0.43 mmol) of methoxylamine hydrochloride were heated and stirred in 3 ml of pyridine at 100° C. for 80 min. The solvent was distilled off under the reduced pressure, the residue was dissolved in chloroform, washed with water, and dried over sodium sulphate. The solvent was distilled off under the reduced pressure, the residue was purified by silica gel chromatography (developer:chloroform/MeOH=40/1) to obtain 196 mg of the titled compound as pale yellow powder (yield 92% ). This has the following NMR spectrum, and is a mixture of isomers based on syn and anti of an oxime. Compound Number: 73 $\delta$ ppm (CDCl$_3$): 0.79 (3H, t, J=7 Hz), 1.24 (2H, sextet, J=7 Hz), 1.51 (2H, quintet, J=7 Hz), 2.02, 2.07 (3H, two s), 2.26, 2.44 (3H, two s), 2.49 (2H, t, J=7 Hz), 4.02, 4.04 (3H, two s), 5.57, 5.65 (2H, two s), 6.8–7.1 (4H, m), 7.2–7.6 (3H, m), 7.9 (1H, m)

EXAMPLE 24

Preparation of 1-[(2'-(tetrazol-5-yl)biphenyl4-yl)methyl]-4-methoxyimino-2-n-propyl-1H-naphthimidazol-9-one (Compound No. 70)

According to the same manner as that described in Example 23, the titled compound was synthesized from 1-[(2'-(tetrazol-5-yl)biphenyl-4-yl)methyl]-2-n-propyl-1H-naphthimidazol-4,9-dione (Compound No. 18) obtained in Example 5. This has the following NMR spectrum. Compound Number: 70 $\delta$ ppm (CDCl$_3$): 0.85 (3H, t, J=7 Hz), 1.60 (2H, sextet, J=7 Hz), 2.54 ( 2H, t, J=7 Hz), 4.07, 4.17 (3H, two s), 5.65, 5.73 (2H, two s), 6.8–8.0 (10H, m), 8.14, 8.28 (1H, two d, J= 7 Hz), 8.34, 9.00 (1H, two d, J=8 Hz)

EXAMPLE 25

Following the procedures of the preceding examples, the methods of the charts, and analogous procedures well-known to those of ordinary skill in the art, the following compounds are prepared:

29) 1-[(2'-(Tetrazol-5-yl)biphenyl-4-yl)methyl]-2-n-butyl-5,6-dimethoxy-1H-benzimidazol-4,7-dione 33) 1-[(2'-(Tetrazol-5-yl)biphenyl-4-yl)methyl]-2-n-butyl-5-methyl- 6-carboxymethyl- 1H-benzimidazol-4,7-dione, 37) 1-[(2'-(Tetrazol-5-yl)biphenyl-4-yl)methyl]-2-n-butyl-5-methyl- 6-carboxy-1H-benzimidazol- 4,7-dione, 41) 1-[(2'-(Tetrazol-5-yl)biphenyl-4-yl)methyl]-2-n-butyl-5-methyl- 6-(N,N-dimethyl)carbamoyl- 1H-benzimidazol-4,7-dione, 53) 1-[(2'-(Tetrazol-5-yl)biphenyl-4-yl)methyl]-2-n-butyl-5-methyl- 6-( 2-carboxy)ethyl-1H-benzimidazol-4,7-dione, 59) 1-[(2'-(Tetrazol-5-yl)biphenyl-4-yl)methyl]-2-n-butyl-5-methyl- 6-( 2-hydroxyethyl)-1H-benzimidazol-4, 7-dione, 74) 1-[(2'-(Tetrazol-5-yl)biphenyl-4-yl)methyl]-2-n-butyl-4-ethylidene-1H-naphtimidazol-9-one, 75) 1-[(2'-(Tetrazol-5-yl)biphenyl-4-yl)methyl]-2-n-butyl-4-benzylidene- 1H-naphtimidazol-9-one, 76) 1-[(2'-(Tetrazol-5-yl)biphenyl-4-yl)methyl]-2-n-butyl-4-( 2,2-dimethyl)propylidene- 1H-naphtimidazol-9-one, 77) 1-[(2'-(Tetrazol-5-yl)biphenyl-4-yl)methyl]-2-n-butyl-4-ethylidene- 5,6-dimethyl- 1H-benzimidazol-7-one, 78) 1-[(2'-(Tetrazol-5-yl)biphenyl-4-yl)methyl]-2-n-butyl-4-benzylidene- 5-methyl- 6-(2-carboxy)ethyl-1H-benzimidazol-7-one, 79) 1-[(2'-(Tetrazol-5-yl)biphenyl-4-yl)methyl]-2-n-butyl-4-(2,2-dimethyl)propylidene-5-methyl-6-(2-hydroxy)ethyl-1H-benzimidazol-7-one, 80) 1-[(2'-(Tetrazol-5-yl)biphenyl-4-yl)methyl]-2-n-butyl-1H-naphtimidazol-4,9dione, methylhydrazone, 81) 1-[(2'-(Tetrazol-5-yl)biphenyl-4-yl)methyl]-2-n-butyl-5,6-dimethyl-1H-benzimidazol-4,7-dione phenylhydrazone.

We claim:

1. An imidazobenzoquinone represented by the general formula:

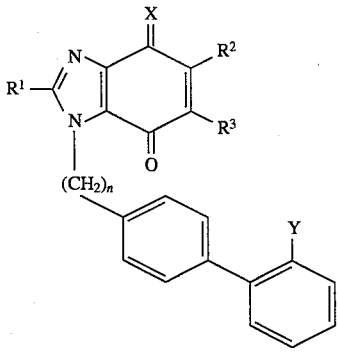

wherein

R$^1$ is hydrogen atom, a C$_1$–C$_8$ alkyl group, a C$_2$–C$_8$ alkenyl group, a C$_2$–C$_8$ alkynyl group, or a —CF$_3$ group;

X is oxygen atom or a group of the formula N—OR$^6$, N—NHR$^5$, or CR$^7$R$^8$;

Y is a 1H-tetrazol-5-yl group or an alkali metal salt thereof, a —CO$_2$R$^4$ group, a —CONR'R" group or a —CONHSO$_2$R$^5$ group;

R$^2$ and R$^3$ are independently hydrogen atom, a C$_1$–C$_8$ alkyl group, a C$_1$–C$_8$ alkoxy group, —CN, a —CO$_2$R$^4$ group, a —CONR'R" group or a —CONHSO$_2$R$^5$ group;

R$^4$ is hydrogen atom, alkali metal or a C$_1$–C$_8$ alkyl group;

R$^5$ is a C$_1$–C$_8$ alkyl group, or a C$_3$–C$_{10}$ cycloalkyl group;

R$^6$ is hydrogen atom or a C$_1$–C$_8$ alkyl group;

R$^7$ and R$^8$ are independently hydrogen, C$_1$–C$_8$ alkyl, C$_2$–C$_8$ alkenyl, C$_2$–C$_8$ alkynyl, CF$_3$, aryl, or aralkyl;

R' and R" are independently hydrogen atom or a C$_1$–C$_8$ alkyl group; and n is 0, 1 or 2, or a pharmacologically acceptable ester or salt thereof.

2. A composition for preventing or treating hypertension or congestive heart failure which comprises as an active ingredient an imidazobenzoquinone of claim 1 and a pharmaceutically acceptable carrier therefor.

3. A compound of claim 1, selected from the group consisting of:

25) 1-[(2'-Carboxybiphenyl-4-yl)methyl]-2-n-butyl-1H-benzimidazol-4,7dione, 26) 1-[(2'-Carboxybiphenyl-4-yl)methyl]-2-n-butyl-5,6-dimethyl-1H-benzimidazol- 4,7-dione, 27) 1-[(2'-(Tetrazol-5-yl)biphenyl-4-yl)methyl]-2-n-butyl-5,6-dimethyl-1H-benzimidazol-4,7-dione, 28) 1-[(2'-Carboxybiphenyl-4-yl)methyl]-2-n-butyl-5,6-dimethoxy-1H-benzimidazol- 4,7 -dione, 29) 1-[(2'-(Tetrazol-5-yl)biphenyl-4-yl)methyl]-2-n-butyl-5,6-dimethoxy-1H-benzimidazol-4,7-dione, 30) 1-[(2'-Carboxybiphenyl-4-yl)methyl]-2-n-butyl-5,6-dihydroxymethyl-1H-benzimidazol- 4,7-dione, 31) 1-[(2'-(Tetrazol-5-yl)biphenyl-4-yl)methyl]-2-n-butyl-5,6-dihydroxymethyl- 1H-benzimidazol-4,7-dione, 32) 1-[(2'-Carboxybiphenyl-4-yl)methyl]-2-n-butyl-5-methyl-6-carboxymethyl- 1H-benzimidazol-4,7-dione, 33) 1-[(2'-(Tetrazol-5-yl)biphenyl-4-yl)methyl]-2-n-butyl-5-methyl- 6-carboxymethyl-1H-benzimidazol-4,7-dione, 34) 1-[(2'-Carboxybiphenyl-4-yl)methyl]-2-n-butyl-5-carboxymethyl-6-methyl- 1H-benzimidazol-4,7-dione, 35) 1-[(2'-(Tetrazol-5-yl)biphenyl-4-yl)methyl]-2-n-butyl-5-carboxymethyl-6-methyl- 1H-benzimidazol-4,7-dione, 36) 1-[(2'-Carboxybiphenyl-4-yl)methyl]-2-n-butyl-5-methyl-6-carboxy- 1H-benzimidazol- 4,7-dione, 37) 1-[(2'-(Tetrazol-5-yl)biphenyl-4-yl)methyl]-2-n-butyl-5-methyl- 6-carboxy- 1H-benzimidazol-4,7-dione, 38) 1-[(2'-Carboxybiphenyl-4-yl)methyl]-2-n-butyl-5-carboxy-6-methyl-1H-benzimidazol-4,7-dione, 39) 1-[(2'-(Tetrazol-5-yl)biphenyl-4-yl)methyl]-2-n-butyl-5-carboxy-6-methyl- 1H-benzimidazol-4,7-dione, 40) 1-[(2'-Carboxybiphenyl-4-yl)methyl]-2-n-butyl-5-methyl-6-(N,N-dimethyl)carbamoyl- 1H-benzimidazol-4,7-dione, 41) 1-[(2'-(Tetrazol-5-yl)biphenyl-4-yl)methyl]-2-n-butyl-5-methyl- 6-(N,N-dimethyl)carbamoyl- 1H-benzimidazol-4,7-dione, 42) 1-[(2'-Carboxybiphenyl-4-yl)methyl]-2-n-butyl-5-(N,N-dimethyl)carbamoyl- 6-methyl-1H-benzimidazol-4, 7-dione, 43) 1-[(2'-(Tetrazol-5-yl)biphenyl-4-yl)methyl]-2-n-butyl-5-(N,N-dimethyl)carbamoyl- 6-methyl-1H-benzimidazol-4,7-dione, 44) 1-[(2'-Carboxybiphenyl-4-yl)methyl]-2-n-butyl-5-methyl-6-cyano- 1H-benzimidazol- 4,7-dione, 45) 1-[(2'-(Tetrazol-5-yl)biphenyl-4-yl)methyl]-2-n-butyl-5-methyl-6-cyano-1H-benzimidazol-4,7-dione, 46) 1-[(2'-Carboxybiphenyl-4-yl)methyl]-2-n-butyl-5-cyano-6-methyl- 1H-benzimidazol-4,7-dione, 47) 1-[(2'-(Tetrazol-5-yl)biphenyl-4-yl)methyl]-2-n-butyl-5-cyano-6-methyl-1H-benzimidazol-4,7-dione, 48) 1-[(2'-Carboxybiphenyl-4-yl)methyl]-2-n-butyl-5,6-dicyano-1H-benzimidazol- 4,7-dione, 49) 1-[(2'-(Tetrazol-5-yl)biphenyl-4-yl)methyl]-2-n-butyl-5,6-dicyano- 1H-benzimidazol-4,7 -dione, 50) 1-[(2'-Carboxybiphenyl-4-yl)methyl]-2-n-butyl-5-methyl- 6-(N-methanesulfonyl)carbamoyl- 1H-benzimidazol-4,7-dione, 51) 1-[(2'-(Tetrazol-5-yl)biphenyl-4-yl)methyl]-2-n-butyl-5-methyl-6-(N-methanesulfonyl)carbamoyl-1H-benzimidazol-4,7-dione, 52) 1-[(2'-Carboxybiphenyl-4-yl)methyl]-2-n-butyl-5-methyl-6-(2-carboxy)ethyl- 1H-benzimidazol-4,7-dione, 53) 1-[(2'-(Tetrazol-5-yl)biphenyl-4-yl)methyl]-2-n-butyl-5-methyl-6-( 2-carboxy)ethyl- 1H-benzimidazol-4,7-dione, 54) 1-[(2'-Carboxybiphenyl-4-yl)methyl]-2-n-butyl-5-methyl-6-( 3-carboxy)propyl- 1H-benzimidazol-4,7-dione, 55) 1-[(2'-(Tetrazol-5-yl)biphenyl-4-yl)methyl]-2-n-butyl-5-methyl-6-( 3-carboxy)propyl- 1H-benzimidazol-4,7-dione, 56) 1-[(2'-Carboxybiphenyl-4-yl)methyl]-2-n-butyl-5-methyl-6-( 4-carboxy)butyl-1H-benzimidazol-4,7-dione, 57) 1-[(2'-(Tetrazol-5-yl)biphenyl-4-yl)methyl]-2-n-butyl-5-methyl-6-( 4-carboxy)butyl- 1H-benzimidazol-4,7-dione, 58) 1-[(2'-Carboxybiphenyl-4-yl)methyl]-2-n-butyl-5-methyl-6-( 2-hydroxyethyl)- 1H-benzimidazol-4,7-dione, 59) 1-[(2'-(Tetrazol-5-yl)biphenyl-4-yl)methyl]-2-n-butyl-5-methyl-6-( 2-hydroxyethyl)- 1H-benzimidazol-4,7-dione, 60) 1-[(2'-Carboxybiphenyl-4-yl)methyl]-2-n-butyl-5-methyl-6-(3-hydroxpropyl)-1H-benzimidazol-4,7-dione, 61) 1-[(2'-(Tetrazol-5-yl)biphenyl-4-yl)methyl]-2-n-butyl-5-methyl-6-( 3-hydroxypropyl)-1H-benzimidazol-4,7-dione, 62) 1-[(2'-Carboxybiphenyl-4-yl)methyl]-2-n-butyl-5-methyl-6-(4-hydroxybutyl)-1H-benzimidazol-4,7-dione, 63) 1-[(2'-(Tetrazol-5-yl)biphenyl-4-yl)methyl]-2-n-butyl-5-methyl-6-(4-hydroxybutyl-1H-benzimidazol-4,7-dione, 66) 1-[(2'-(Tetrazol-5-yl)biphenyl-4-yl)methyl]-2-ethyl-5,6-dimethyl- 1H-benzimidazol- 4,7-dione, 67) 1-[(2'-(Tetrazol-5-yl)biphenyl-4-yl)methyl]-2-n-propyl-5,6-dimethyl-1H-benzimidazol-4,7-dione, 68) 1-[(2'-(Tetrazol-5-yl)biphenyl-4-yl)methyl]-2-n-pentyl-5,6-dimethyl- 1H-benzimidazol-4,7-dione, 69) 1-[(2'-(Tetrazol-5-yl)biphenyl-4-yl)methyl]-2-n-hexyl-5,6-dimethyl-1H-benzimidazol-4,7-dione, 72) 1-[(2'-(Tetrazol-5-yl)biphenyl-4-yl)methyl]-5,6-dimethyl-4-methoxyimino- 2-n-propyl-1H-benzimidazol-7-one, 73) 1-[(2'-(Tetrazol-5-yl)biphenyl-4-yl)methyl]-2-n-butyl-5,6-dimethyl- 4-methoxyimino- 1H-benzimidazol-7-one, 77) 1-[(2'-(Tetrazol-5-yl)biphenyl-4yl)methyl]-2-n-butyl-4-ethylidene- 5,6-dimethyl-1H-benzimidazol-7-one, 78) 1-[(2'-(Tetrazol-5-yl)biphenyl-4-yl)methyl]-2-n-butyl-4-benzylidene- 5-methyl- 6-(2-carboxy)ethyl-1H-benzimidazol-7-one, 79) 1-[(2'-(Tetrazol-5-yl)biphenyl-4-yl)methyl]-2-n-butyl-4-(2,2dimethyl)propylidene-5-methyl-6-(2-hydroxy)ethyl-1H -benzimidazol-7-one, and 81) 1-[(2'-(Tetrazol-5-yl)biphenyl-4-yl)methyl]-2-n-butyl-5,6-dimethyl-1H-benzimidazol-4,7-dione phenylhydrazone.

4. A compound of claim 1, wherein $R^1$ is $C_3$–$C_7$ alkyl;

X is oxygen;

Y is a 1H-tetrazol-5-yl group or an alkali metal salt thereof or —$CO_2H$; and n is 1.

5. A compound of claim 4, selected from:

1-[(2'-(Tetrazol-5-yl)biphenyl-4-yl)methyl]-2-n-butyl-1H-5,6-dimethyl-1H-benzimidazol-7-one; and 1-[(2'-(Tetrazol-5-yl)biphenyl-4-yl)methyl]-2-n-pentyl-1H-5,6-dimethyl- 1H-benzimidazol-7-one.

* * * * *